US012766164B2

(12) United States Patent
De Marchi et al.

(10) Patent No.: US 12,766,164 B2
(45) Date of Patent: Oct. 20, 2026

(54) COMPOSITIONS AND METHODS USING ADENOSYLCOBALAMIN

(71) Applicant: SOCIETE DES PRODUITS NESTLE S.A., Vevey (CH)

(72) Inventors: Umberto De Marchi, Corminboeuf (CH); Jerome Feige, Crissier (CH); Aurelie Hermant, Lausanne (CH); Sonia Karaz, Epalinges (CH)

(73) Assignee: Societe des Produits Nestle S.A., Vevey (CH)

( * ) Notice: Subject to any disclaimer, the term of this patent is extended or adjusted under 35 U.S.C. 154(b) by 596 days.

(21) Appl. No.: 17/754,071

(22) PCT Filed: Sep. 23, 2020

(86) PCT No.: PCT/EP2020/076486

§ 371 (c)(1),
(2) Date: Mar. 23, 2022

(87) PCT Pub. No.: WO2021/058514

PCT Pub. Date: Apr. 1, 2021

(65) Prior Publication Data

US 2022/0323479 A1 Oct. 13, 2022

Related U.S. Application Data

(60) Provisional application No. 62/905,508, filed on Sep. 25, 2019.

(51) Int. Cl.

| | |
|---|---|
| ***A61K 31/714*** | (2006.01) |
| ***A61P 3/00*** | (2006.01) |
| ***A61P 21/00*** | (2006.01) |

(52) U.S. Cl.
CPC .............. *A61K 31/714* (2013.01); *A61P 3/00* (2018.01); *A61P 21/00* (2018.01)

(58) Field of Classification Search
None
See application file for complete search history.

(56) References Cited

U.S. PATENT DOCUMENTS

| | | | | |
|---|---|---|---|---|
| 2003/0018009 | A1 | 1/2003 | Collins | |
| 2008/0045448 | A1 | 2/2008 | Vinitsky | |
| 2008/0113900 | A1 | 5/2008 | Brasch et al. | |
| 2012/0231089 | A1 * | 9/2012 | Vinitsky | A61P 25/00 424/722 |
| 2015/0182548 | A1 | 7/2015 | Armstrong | |
| 2015/0306128 | A1 | 10/2015 | Armstrong | |
| 2017/0274002 | A1 | 9/2017 | Daniels et al. | |
| 2018/0161299 | A1 * | 6/2018 | Bortz | A61K 31/202 |
| 2018/0256538 | A1 | 9/2018 | Rinsch et al. | |
| 2018/0353534 | A1 | 12/2018 | Pannerec et al. | |
| 2019/0008883 | A1 | 1/2019 | Andreux et al. | |

FOREIGN PATENT DOCUMENTS

| | | | | |
|---|---|---|---|---|
| AU | 2013216665 | | 3/2014 | |
| JP | 2019034902 | A | 3/2019 | |
| WO | WO-03000010 | A2 * | 1/2003 | A23C 9/158 |
| WO | WO-2005094842 | A1 * | 10/2005 | A61P 29/00 |
| WO | WO-2011149337 | A1 * | 12/2011 | A61K 31/155 |
| WO | WO-2017108419 | A1 * | 6/2017 | A61K 31/714 |
| WO | 2018105550 | A1 | 6/2018 | |

OTHER PUBLICATIONS

Japanese Office Action for Appl No. 2022-515762 dated Sep. 10, 2024, 6 pages.
Chinese Office Action for Chinese Appl No. 202080064770.6 dated Jun. 14, 2023.
Marzetti et al., "Sarcopenia of Aging: Underlying Cellular Mechanisms and Protection by Calorie Restriction", Biofactors, vol. 35, Issue No. 1, 2009, pp. 28-35.
Japanese Office Action for Appl No. 2025-060259 dated Jul. 21, 2026, 3 pages not in English.

* cited by examiner

*Primary Examiner* — Michelle F. Paguio Frising
(74) *Attorney, Agent, or Firm* — K&L Gates LLP

(57) ABSTRACT

A composition effective for restoring mitochondrial and other cellular function and/or increasing mitochondrial energy in one or more cells contains adenosylcobalamin. Other aspects are directed to method of improving in a physiological state linked to metabolic fatigue in one or more cells and/or reducing fatigue in an individual; method of treating, reducing an incidence of, and/or reducing a severity of a chronic illness and/or of a mitochondria-related disease or condition associated with altered mitochondrial function or a reduced mitochondrial density.

3 Claims, 6 Drawing Sheets

COMPOSITIONS AND METHODS USING ADENOSYLCOBALAMIN

CROSS REFERENCE TO RELATED APPLICATIONS

The present application is a National Stage of International Application No. PCT/EP2020/076486, filed on Sep. 23, 2020. which claims priority to U.S. Provisional Patent Application No. 62/905,508, filed on Sep. 25, 2019, the entire contents of which are being incorporated herein by reference.

BACKGROUND

The present disclosure generally relates to compositions and methods that increase cellular energy and/or treat or prevent mitochondria related disease or condition, for example by increasing ATP production in the cells, reducing oxidative stress and/or enhancing mitochondrial function in an individual.

Adenosine triphosphate (ATP) is a complex organic chemical that provides energy to drive many processes in living cells, e.g. muscle contraction, nerve impulse propagation, and chemical synthesis. Found in all forms of life, ATP is often referred to as the "molecular unit of currency" of intracellular energy transfer. When consumed in metabolic processes, it converts either to adenosine diphosphate (ADP) or to adenosine monophosphate (AMP). It is also a precursor to DNA and RNA, and is used as a coenzyme. ATP is also a substrate of adenylate cyclase, most commonly in G protein-coupled receptor signal transduction pathways and is transformed to second messenger, cyclic AMP, which is involved in triggering calcium signals by the release of calcium from intracellular stores. This form of signal transduction is particularly important in brain function, although it is involved in the regulation of a multitude of other cellular processes.

Mitochondria are the primary source of aerobic energy production in mammalian cells and the key organelle responsible for cellular energy production. Loss of function in mitochondria can result in the excess fatigue and other symptoms that are common complaints in almost every chronic disease. At the molecular level, a reduction in mitochondrial function may occur, resulting in a reduced efficiency of oxidative phosphorylation and a reduction in production of adenosine-5'-triphosphate (ATP). Clinical trials have shown the utility of using oral replacement supplements, such as 1-carnitine, alpha-lipoic acid, coenzyme $Q_{10}$, NADH, membrane phospholipids, and other supplements. Combinations of these supplements can reduce significantly the fatigue and other symptoms associated with chronic disease and can naturally restore mitochondrial function, even in long-term patients with intractable fatigue.

Fatigue is considered a multidimensional sensation that is perceived to be a loss of overall energy and an inability to perform even simple tasks without exertion. Although mild fatigue can be caused by a number of conditions, including depression and other psychological conditions, moderate to severe fatigue involves cellular energy systems. At the cellular level, moderate to severe fatigue is related to loss of mitochondrial function and diminished production of ATP. Intractable fatigue lasting more than 6 months that is not reversed by sleep (chronic fatigue) is the most common complaint of patients seeking general medical care. Chronic fatigue is also an important secondary condition in many clinical diagnoses, often-preceding patients' primary diagnoses.

Moreover, as a result of aging and chronic diseases, oxidative damage to mitochondrial membranes impairs mitochondrial function. As an example, individuals with chronic fatigue syndrome present with evidence of oxidative damage to DNA and lipids, such as oxidized blood markers and oxidized membrane lipids that is indicative of excess oxidative stress.

SUMMARY

In view of the experimental data disclosed later herein, the present inventors believe that adenosylcobalamin (adenosyl B12), contrary to other B12 isomers, increases the ATP-synthase-dependent component of the respiration, potentiates epibatine-stimulated ATP production, thus enhancing the efficiency of mitochondria to produce energy.

Accordingly, in a general embodiment, the present disclosure provides a method of restoring mitochondrial and other cellular function and/or increasing mitochondrial energy in one or more cells, the method comprising administering to an individual in need thereof an effective amount of adenosylcobalamin, in particular by increasing ATP production and mitochondrial respiration.

In an embodiment, the present disclosure provides a method of improving in a physiological state linked to metabolic fatigue in one or more cells and/or reducing fatigue in an individual, the method comprising administering to the individual in need thereof an effective amount of adenosylcobalamin.

In another embodiment, the present disclosure provides a method of treating, reducing an incidence of, and/or reducing a severity of a chronic illness, the method comprising administering to the individual in need thereof an effective amount of adenosylcobalamin.

In an embodiment, at least a portion of the one or more cells are part of at least one body part selected from the group consisting of a liver, a kidney, a brain, a heart, an intestine, a pancreas, an immune cell and a skeletal muscle.

In another embodiment, the present disclosure provides a method of treating, reducing an incidence of, and/or reducing a severity of a mitochondria-related disease or condition associated with altered mitochondrial function or a reduced mitochondrial density, the method comprising orally administering to an individual in need thereof an effective amount of adenosylcobalamin.

The mitochondria-related disease or condition can be selected from the group consisting of stress, physiological ageing, obesity, reduced metabolic rate, metabolic syndrome, diabetes mellitus, complications from diabetes, hyperlipidemia, neurodegenerative disease, cognitive disorder, stress-induced or stress-related cognitive dysfunction, mood disorder, anxiety disorder, age-related neuronal death or dysfunction, chronic kidney disease, kidney failure, chronic heart failure, cardiac rehabilitation, orthopedic rehabilitation, wound healing, recovery from surgery, trauma, infection, cancer, hearing loss, macular degeneration, myopathies and dystrophies, and combinations thereof.

In a further embodiment, it provides a method of delaying off-set of metabolic decline, decreasing oxidative stress, maintaining immune function and/or maintaining cognitive function in a healthy older adult, the method comprising orally administering to the healthy older adult an effective amount of adenosylcobalamin It also relates to a method of enhancing metabolizing of reactive oxygen species, improving glucose control in an individual with at least one of obesity or diabetes, the method comprising orally administering to the individual an effective amount of adenosylcobalamin.

An advantage of one or more embodiments provided by the present disclosure is to boost healthy aging of cells.

Another advantage of one or more embodiments provided by the present disclosure is to help off-set slowing of the metabolism associated with aging.

And another advantage of one or more embodiments provided by the present disclosure is to help increase fatty acids metabolism.

Yet another advantage of one or more embodiments provided by the present disclosure is to help the body to metabolize fat and increase lean body mass.

An advantage of one or more embodiments provided by the present disclosure is to help maintain heart health.

Another advantage of one or more embodiments provided by the present disclosure is to help support healthy LDL-cholesterol and fatty acid levels in the blood.

Yet another advantage of one or more embodiments provided by the present disclosure is to help reduce oxidative stress on the body.

Additional features and advantages are described herein and will be apparent from the following Figures and Detailed Description.

BRIEF DESCRIPTION OF DRAWINGS

FIG. 1. Adenosyl B12 increases the ATP-synthase-dependent component of the respiration in stimulated human skeletal muscle myotubes. Myotubes were treated for 3 h with or without (control) adenosyl B12 at the indicated concentrations. Then oxygen consumption rate was measured and myotubes were stimulated with epibatidine (10 μM). Statistical evaluation of the effect of adenosyl B12 on the stimulated ATP-synthase-dependent component of the respiration, calculated by inhibiting mitochondrial ATP synthase with oligomycin (2.5 μg/ml). Graph shows the average of 16 cellular assays. Results are expressed as mean+/−SEM. * indicates statistical significant difference vs. control cells (white) at $P<0.05$ (one-way ANOVA test).

FIG. 2. Methyl B12 does not increase the ATP-synthase-dependent component of the respiration in stimulated human skeletal muscle myoblasts. Myotubes were treated for 3 h with or without (control) methyl B12 at the indicated concentrations. Then oxygen consumption rate was measured and myotubes were stimulated with epibatidine (10 μM). Statistical evaluation of the effect of methyl B12 on the stimulated ATP-synthase-dependent component of the respiration, calculated by inhibiting mitochondrial ATP synthase with oligomycin (2.5 mg/ml). Graph shows the average of 16 cellular assays. Results are expressed as mean+/−SEM. NS, not significant (one-way ANOVA test).

FIG. 3. Adenosyl B12, but not methyl B12 potentiates epibatine-stimulated ATP production in human skeletal muscle myotubes, during acute treatment. Human myotubes were treated for 3 h with adenosyl B12 or methyl B12, at the indicated concentrations. Statistical evaluation of the effect of B12 isoforms on ATP production, evoked by epibatidine. Graph shows the average of 3 independent experiments. Results are expressed as mean+/−SEM. * indicates statistical significant difference vs. control cells (white) at $P<0.05$ (one-way ANOVA test).

FIG. 4. Chronic treatment of human skeletal muscle myotubes with Adenosyl B12, but not with methyl B12, potentiates epibatine-stimulated ATP production. Human myotubes were treated for 3 days with adenosyl B12 or methyl B12, at the indicated concentrations. Statistical evaluation of the effect of B12 isoforms on ATP production, evoked by epibatidine. Graph shows the average of 3 independent experiments. Results are expressed as mean+/−SEM. * indicates statistical significant difference vs. control cells (white) at $P<0.05$ (one-way ANOVA test).

FIG. 5. Adenosyl-B12 specifically shows gene expression signature of oxidative phosphorylation genes in skeletal muscle.

DETAILED DESCRIPTION

Definitions

Figure 1:
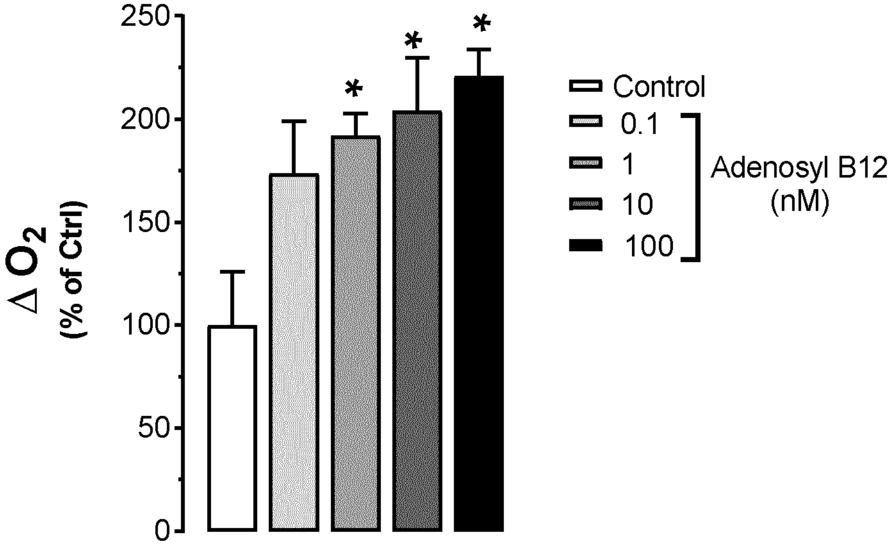
FIGS. 1-4 are graphs of data from the experimental example disclosed herein.

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 50 wt. % of the referenced components, preferably at least 75 wt. % of the referenced components, more preferably at least 85 wt. % of the referenced components, most preferably at least 95 wt. % of the referenced components.

The term "and/or" used in the context of "X and/or Y" should be interpreted as "X," or "Y," or "X and Y." Similarly, "at least one of X or Y" should be interpreted as "X," or "Y," or "X and Y." For example, "at least one of mental performance or muscle performance" should be interpreted as "mental performance or muscle performance," or "muscle performance," or "both mental performance and muscle performance."

Where used herein, the terms "example" and "such as," particularly when followed by a listing of terms, are merely exemplary and illustrative and should not be deemed to be exclusive or comprehensive. As used herein, a condition "associated with" or "linked with" another condition means the conditions occur concurrently, preferably means that the conditions are caused by the same underlying condition, and most preferably means that one of the identified conditions is caused by the other identified condition.

The terms "food," "food product" and "food composition" mean a product or composition that is intended for ingestion by an individual such as a human and provides at least one nutrient to the individual. A food product typically includes at least one of a protein, a lipid, a carbohydrate and optionally includes one or more vitamins and minerals. The compositions of the present disclosure, including the many embodiments described herein, can comprise, consist of, or consist essentially of the elements disclosed herein, as well as any additional or optional ingredients, components, or elements described herein or otherwise useful in a diet.

As used herein, the term "isolated" means removed from one or more other compounds or components with which the compound may otherwise be found, for example as found in nature. For example, "isolated" preferably means that the identified compound is separated from at least a portion of the cellular material with which it is typically found in nature. In an embodiment, an isolated compound is pure, i.e., free from any other compound.

As used herein, an "effective amount" is an amount that prevents a deficiency, treats a disease or medical condition in an individual, or, more generally, reduces symptoms, manages progression of the disease, or provides a nutritional, physiological, or medical benefit to the individual. The relative terms "improved," "increased," "enhanced" and the like refer to the effects of the composition disclosed herein. As used herein, "promoting" refers to enhancing or inducing relative to the level before administration of the composition disclosed herein.

The term "unit dosage form," as used herein, refers to physically discrete units suitable as unitary dosages for human and animal subjects, each unit containing a predetermined quantity of the composition disclosed herein in an amount sufficient to produce the desired effect, preferably in association with a pharmaceutically acceptable diluent, carrier or vehicle. The specifications for the unit dosage form depend on the particular compounds employed, the effect to be achieved, and the pharmacodynamics associated with each compound in the host. In some embodiments, the unit dosage form can be a predetermined amount of the active compounds in a serving of a food product, a predetermined amount of powder in a sachet, a predetermined amount of the active compounds in a capsule or a tablet, or a predetermined amount of the active compounds in a predetermined volume of liquid, preferably a therapeutically or prophylactically effective amount or a predetermined portion of a therapeutically or prophylactically effective amount.

A "subject" or "individual" is a mammal, preferably a human. The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

"As used herein, "frailty" is defined as a clinically recognizable state of increased vulnerability resulting from aging-associated decline in reserve and function across multiple physiologic systems such that the ability to cope with everyday or acute stressors is compromised. A pre-frail stage, in which one or two of these criteria are present, identifies a high risk of progressing to frailty.

"Overweight" is defined for a human as a body mass index (BMI) between 25 and 30 kg/m$^2$. "Obese" is defined for a human as a BMI of at least 30 kg/m$^2$, for example 30-39.9 kg/m$^2$. "Weight loss" is a reduction of the total body weight. Weight loss may, for example, refer to the loss of total body mass in an effort to improve one or more of health, fitness or appearance.

"Diabetes" encompasses both the type I and type II forms of the disease. Non-limiting examples of risk factors for diabetes include: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

As used herein, the term "metabolic syndrome" refers to a combination of medical disorders that, when occurring together, increase the risk of developing cardiovascular disease and diabetes. It affects one in five people in the United States and prevalence increases with age. Some studies have shown the prevalence in the United States to be an estimated 25% of the population. In accordance with the International Diabetes Foundation consensus worldwide definition (2006), metabolic syndrome is central obesity plus any two of the following:

Raised triglycerides: >150 mg/dL (1.7 mmol/L), or specific treatment for this lipid abnormality;

Reduced HDL cholesterol: <40 mg/dL (1.03 mmol/L) in males, <50 mg/dL (1.29 mmol/L) in females, or specific treatment for this lipid abnormality;

Raised blood pressure: systolic BP>130 or diastolic BP>85 mm Hg, or treatment of previously diagnosed hypertension; and Raised fasting plasma glucose: (FPG)>100 mg/dL (5.6 mmol/L), or previously diagnosed type 2 diabetes.

As used herein, "neurodegenerative disease" or "neurodegenerative disorder" refers to any condition involving progressive loss of functional neurons in the central nervous system. In an embodiment, the neurodegenerative disease is associated with age-related cell death. Non-limiting examples of neurodegenerative diseases include Alzheimer's disease, Parkinson's disease, Huntington's disease, amyotrophic lateral sclerosis (also known as ALS and as Lou Gehrig's disease), AIDS dementia complex, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Kennedy's disease, Krabbe disease, Lyme disease, Machado- Joseph disease, multiple sclerosis, multiple system atrophy, neuroacanthocytosis, Niemann-Pick disease, Pick's disease, primary lateral sclerosis, progressive supranuclear palsy, Refsum disease, Sandhoff disease, diffuse myelinoclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome. As used herein, "cognitive function" refers to any mental process that involves symbolic operations, e.g., perception, memory, attention, speech comprehension, speech generation, reading comprehension, creation of imagery, learning, and reasoning, preferably at least memory.

Methods for measuring cognitive function are well-known and can include, for example, individual or battery tests for any aspect of cognitive function. One such test is the Prudhoe Cognitive Function Test by Margallo-Lana et al. (2003) J. Intellect. Disability Res. 47:488-492. Another such test is the Mini Mental State Exam (MMSE), which is designed to assess orientation to time and place, registration, attention and calculation, recall, language use and comprehension, repetition, and complex commands. As used herein, a "cognitive disorder" refers to any condition that impairs cognitive function. Non-limiting examples of a cognitive disorder include delirium, dementia, learning disorder, attention deficit disorder (ADD), and attention deficit hyperactivity disorder (ADHD). A "stress-induced or stress-related cognitive dysfunction" refers to a disturbance in cognitive function that is induced or related to stress.

As used herein, a "mood disorder" (also known as an affective disorder) refers to a disturbance in emotional state, such as is set forth in the Diagnostic and Statistical Manual of Mental Disorders, published by the American Psychiatric Association. Non-limiting examples of mood disorders include major depression, postpartum depression, dysthymia, and bipolar disorder. A "stress-induced or stress-related mood disorder" refers to a disturbance in emotional state that is induced or related to stress. Such mood disorders are sometimes referred to as reactive mood disorders and are distinguished from other mood disorders, e.g., "organic" mood disorders that are due to a medical or physical condition rather than a psychiatric illness.

As used herein, an "anxiety disorder" refers to a dysfunctional state of fear and anxiety, e.g., fear and anxiety that is out of proportion to a stressful situation or the anticipation of a stressful situation. Non-limiting examples of anxiety disorders include generalized anxiety disorder, panic disorder, panic disorder with agoraphobia, agoraphobia, social anxiety disorder, obsessive-compulsive disorder, and post-traumatic stress disorder. A "stress-induced or stress-related anxiety disorder" refers to a dysfunctional state of fear and anxiety that is induced or related to stress. Such anxiety disorders are sometimes referred to as reactive anxiety disorders and are distinguished from other anxiety disorders, e.g., "organic" anxiety disorders that are due to a medical or physical condition rather than a psychiatric illness.

As used herein, "metabolic fatigue" means reduced mitochondrial function in one or more cells (e.g., one or more of liver, kidney, brain, a heart, an intestine, a pancreas, an immune cell or skeletal muscle cell).

EMBODIMENTS

Vitamin B12 (also known as cobalamin) is a class of cobalt-containing hydrosoluble vitamins which cannot be synthesised by the human body and must therefore be acquired from food or synthesised by the gut microbiota. The vitamin B12 class may refer to several chemical forms of vitamin B12, depending on the upper axial ligand of the cobalt ion. These are Cyanocobalamin (R=—CN); Hydroxocobalamin (R=—OH); Methylcobalamin (R=—CH3), andAdenosylcobalamin (R=-5'-deoxyadenosyl).

The vitamin B12 pool in the human body is composed of several forms: cyanocobalamin, which is inactive and requires conversion for activity, and methylcobalamin and adenosylcobalamin, which are the metabolically active forms of vitamin B12.

Two enzymes are known to rely on vitamin B12 as a cofactor: methionine synthase and methylmalonylCoA mutase. Methionine synthase is a cytoplasmic enzyme relying on methyl-cobalamine to convert homocysteine to methionine. It thereby plays a critical role in providing S-adenosylmethionine (SAM) as a methylation donor and preventing the toxic accumulation of homocysteine. Low SAM levels and high homocysteine levels observed upon severe vitamin B12 deficiency impair myelination of peripheral nerves and the spinal cord. Methionine synthase also catalyses the activation of 5-methyl-tetrahydrofolate into the bioactive tetrahydrofolate, which is required for 1-carbon metabolism and DNA synthesis, and thus for efficient red blood cell proliferation. MethylmalonylCoA mutase is a mitochondrial enzyme relying on adenosyl-cobalamine to convert methyl-malonylCoA to succinylCoA, which subsequently enters the TCA cycle. It is implicated in the degradation of branched-chain amino acids and odd-chain length fatty acids, and is essential during embryonic life to control neurological development, but is not vital in adult life The adenosylcobalamin of the invention may be in the form of semi-synthetic derivative.

In another embodiment, the adenosylcobalamin may be hydroxocobalamin and/or cyanocobalamin which can be converted into adenosylcobalamin.

Vitamin B12 Deficiency

In one embodiment the subject may be vitamin B12 deficient.

The Recommended dietary allowance (RDA) of US adults was set at 2.4 µg per day by the Institute of Medicine, based on an average absorption from food of ~50% (National Academy of Sciences, Institute of Medicine (2000); Dietary Reference Intakes for Thiamin, Riboflavin, Niacin, Vitamin B6, Folate, Vitamin B12, Pantothenic Acid, Biotin and Choline, Chapter 9, pp 306-56). It was noted that the daily requirement varies with body size.

The likelihood of vitamin B12 deficiency in humans may be defined according to the serum vitamin B12 level as follows: <148 picomols/L (<200 picograms/mL) indicates probable deficiency, 148 to 258 picomols/L (201 to 350 picograms/mL) indicates possible deficiency and >258 picomols/L (>350 picograms/mL) indicates that deficiency is unlikely (BMJ, Best Practice, http://bestpractice.bmj.com/best-practice/monograph/822/basics.html). However, because of the lack of a gold standard for determining vitamin B12 levels and related complications regarding active and inactive vitamin B12, assays of serum vitamin B12 are often combined with further biochemical assays or clinical assessment based on presenting symptoms, in order to diagnose vitamin B12 deficiency.

Additional assays which may be performed to give a further indication of a vitamin B12 deficiency include determining the level of, holotranscobalamine, methylmalonic acid and/or homocysteine in a sample isolated from the subject.

Holotranscobalamin refers to vitamin B12 bound to its bioactive serum transporter transcobalamine II. Holotranscobalamin levels may be determined using commercial available assays (e.g. ELISA assays). Low levels of holotranscobalamin are associated with a potential vitamin B12 deficiency.

Methyl-malonic acid (MMA) accumulates with low activity of the vitamin B12-dependent enzyme methylmalonyl-CoA mutase. As such high levels of MMA are associated with vitamin B12 deficiency.

In an embodiment, the individual has high circulating levels of methyl-malonic acid.

Homocysteine accumulates with low activity of the vitamin B12-dependent enzyme methionine synthase. Low High levels of homocysteine are associated with vitamin B12 deficiency. However assays of homocysteine levels can be confounded by folate deficiency.

Adenosylcobalamin may, for example, be provided in the form of a tablet, liquid (e.g. for ingestion, or use in a nasal spray or injection) or transdermal patch. For example, it may be available as a nutritional supplement either on its own or in combination with other supplements.

Oral supplementation typically involves giving 1 to 10 μg up to 100 μg to 2000 μg of adenosylcobalamin daily depending on the format. When administered in the form of oral nutritional supplement the daily amount provides 1 to 10 μg, preferably 1 to 2 μg of adenosylcobalamin. When administrered in the form of supplement, the daily amount provides 100 μg to 2000 μg, preferably 250 μg to 1 mg of adenosylcobalamin.

The present invention may comprise administering a probiotic supplement comprising adenosylcobalamin producing bacteria to a subject.

The probiotic supplement can include any probiotic microorganism(s) which beneficially affect the host subject by improving its intestinal microbial balance to enhance vitamin B12 uptake. The probiotic microorganism can be selected from the group comprising of *Bifidobacterium, Lactobacillus, Streptococcus, Enterococcus* and *Saccharomyces* or mixtures thereof.

The oral adenosyl vitamin B12 supplementation may be in the form of a food or beverage product. The food or beverage product may comprise a probiotic supplement comprising vitamin B12 producing bacteria or other probiotics which can enhance existing microorganisms in the gut that produce vitamin B12 in situ.

Typically, a physician will determine the actual dosage which will be most suitable for an individual subject and it will vary with the age, weight and response of the particular patient. The dosage is such that it is sufficient to provide required levels of active adenosyl vitamin B12.

Methods

Without being bound by theory, it is believed that various types of stress result in stress injury to mitochondria, thereby reducing their ability to perform numerous functions essential to overall cell function. The methods disclosed herein can be useful for treating conditions involving stress injury to mitochondria, which injury may be manifest in any of a number of ways including, but not limited to, mitochondrial disease.

Mitochondrial diseases are the result of either inherited or spontaneous mutations in mitochondrial DNA or nuclear DNA which lead to altered functions of the proteins or RNA molecules that normally reside in mitochondria. Problems with mitochondrial function, however, may only affect certain tissues as a result of factors occurring during development and growth that are not yet fully understood. Even when tissue-specific isoforms of mitochondrial proteins are considered, it is difficult to explain the variable patterns of affected organ systems in the mitochondrial disease syndromes seen clinically.

Mitochondrial diseases result from failures of the mitochondria, specialized compartments present in every cell of the body except red blood cells. Mitochondria are responsible for creating more than 90% of the energy needed by the body to sustain life and support growth. When they fail, less and less energy is generated within the cell. Cell injury and even cell death follow. If this process is repeated throughout the body, whole systems begin to fail, and the life of the person in whom this is happening is severely compromised. Mitochondrial diseases primarily affect children, but adult onset is becoming more recognized.

Diseases of the mitochondria appear to cause the most damage to cells of the brain, heart, liver, skeletal muscles, kidney, and the endocrine and respiratory systems.

Many symptoms in mitochondrial disorders are non-specific. The symptoms may also show an episodic course, with periodic exacerbations. The episodic condition of migraine, as well as myalgia, gastrointestinal symptoms, tinnitus, depression, chronic fatigue, and diabetes, have been mentioned among the various manifestations of mitochondrial disorders in review papers on mitochondrial medicine. In patients with mitochondrial disorders, clinical symptomatology typically occurs at times of higher energy demand associated with physiological stressors, such as illness, fasting, over-exercise, and environmental temperature extremes. Furthermore, psychological stressors also frequently trigger symptomatology, presumably due to higher brain energy demands for which the patient is unable to match with sufficient ATP production.

Depending on which cells are affected, symptoms may include loss of motor control, muscle weakness and pain, gastro-intestinal disorders and swallowing difficulties, poor growth, cardiac disease, liver disease, diabetes, respiratory complications, seizures, visual/hearing problems, lactic acidosis, developmental delays and susceptibility to infection.

Mitochondrial diseases include, without limitation, Alper's disease; Barth syndrome; beta-oxidation defects; carnitine deficiency; carnitine-acyl-carnitine deficiency; chronic progressive external ophthalmoplegia syndrome; co-enzyme Q10 deficiency; Complex I deficiency; Complex II deficiency; Complex III deficiency; Complex IV deficiency; Complex V deficiency; CPT I deficiency; CPT II deficiency; creatine deficiency syndrome; cytochrome c oxidase deficiency; glutaric aciduria type II; Kearns-Sayre syndrome; lactic acidosis; LCHAD (long-chain acyl-CoA dehydrogenase deficiency); Leber's hereditary optic neuropathy; Leigh disease; lethal infantile cardiomyopathy; Luft disease; MAD (medium-chain acyl-CoA dehydrogenase deficiency); mitochondrial cytopathy; mitochondrial DNA depletion; mitochondrial encephalomyopathy, lactic acidosis, and stroke-like symptoms; mitochondrial encephalopathy; mitochondrial myopathy; mitochondrial recessive ataxia syndrome; muscular dystrophies, myoclonic epilepsy and ragged-red fiber disease; myoneurogenic gastrointestinal encephalopathy; neuropathy, ataxia, retinitis pigmentosa, and ptosis; Pearson syndrome; POLG mutations; pyruvate carboxylase deficiency; pyruvate dehydrogenase deficiency; SCHAD (short-chain acyl-CoA dehydrogenase deficiency); and very long-chain acyl-CoA dehydrogenase deficiency.

Accordingly, an aspect of the present disclosure is a composition in a unit dosage form comprising a adenosylcobalamin in an amount effective for treatment or prevention of at least condition selected from the group consisting of stress (e.g., early-life stress and/or effects therefrom), obesity, reduced metabolic rate, metabolic syndrome, diabetes mellitus, hyperlipidemia, neurodegenerative disease, cognitive disorder, stress-induced or stress-related cognitive dysfunction, mood disorder (e.g., stress-induced or stress-related mood disorder), anxiety disorder (e.g., stress-induced or stress-related anxiety disorder) and age-related neuronal death or dysfunction (e.g., age-related neuronal death or dysfunction not attributable to a specific neurodegenerative disease), trauma, infection (e.g. in ICU) or cancer.

Another aspect of the present disclosure is a method of treating at least condition selected from the group consisting of stress (e.g., early-life stress and/or effects therefrom), obesity, reduced metabolic rate, metabolic syndrome, diabetes mellitus, cardiovascular disease, hyperlipidemia, neurodegenerative disease, cognitive disorder, stress-induced or stress-related cognitive dysfunction, mood disorder (e.g., stress-induced or stress-related mood disorder), anxiety disorder (e.g., stress-induced or stress-related anxiety disorder) and age-related neuronal death or dysfunction (e.g., age-related neuronal death or dysfunction not attributable to a specific neurodegenerative disease), trauma, infection (e.g. in ICU) or cancer in an individual having the at least one condition. The method comprises administering to the individual a composition comprising a therapeutically effective amount of adenosylcobalamin.

A further aspect of the present disclosure is a method of preventing at least one condition selected from the group consisting of stress, obesity, reduced metabolic rate, metabolic syndrome, diabetes mellitus, cardiovascular disease, hyperlipidemia, neurodegenerative disease, cognitive disorder, stress-induced or stress-related cognitive dysfunction, mood disorder (e.g., stress-induced or stress-related mood disorder), anxiety disorder (e.g., stress-induced or stress-related anxiety disorder) and age-related neuronal death or dysfunction (e.g., age-related neuronal death or dysfunction not attributable to a specific neurodegenerative disease) trauma, infection (e.g. in ICU) or cancer. The method comprises administering to an individual at risk of the at least one condition a composition comprising a prophylactically effective amount of adenosylcobalamin.

In an embodiment of these methods, the hyperlipidemia that is treated or prevented comprises hypertriglyceridemia. In an embodiment of these methods, the hyperlipidemia that is treated or prevented comprises elevated free fatty acids. In an embodiment of these methods, the age-related neuronal death or dysfunction that is treated or prevented is by administration of the composition to an older adult, such as an elderly individual.

The stress that is treated or prevented can be early-life stress, i.e., stress experienced while under the age of five years from birth. Early-life stress has been reported to have a significant detrimental effect on cognitive performance, including psychological parameters such as increased rates of or susceptibility to depression, anxiety, and abnormal risk-taking behavior. Increased rates of attention-deficit/hyperactivity disorder (ADHD), post-traumatic stress disorder (PTSD), and major depression have been reported in individuals having experienced early-life stress.

Another aspect of the present disclosure is a method of delaying off-set of metabolic decline, decreasing oxidative stress, maintaining immune function and/or maintaining cognitive function in a healthy older adult. The method comprises administering to the healthy older adult an effective amount of adenosylcobalamin.

Another aspect of the present disclosure is a method of improving mitochondrial function in an individual, such as an older adult or an elderly individual. The method comprises administering to the individual an effective amount of adenosylcobalamin.

Yet another aspect of the present disclosure is a method of enhancing metabolizing of reactive oxygen species, improving glucose control in an individual with at least one of obesity or diabetes. The method comprises administering to the individual an effective amount of adenosylcobalamin.

Another aspect of the present disclosure is a method of improving mitochondrial function (preferably to benefit at least one of metabolism or strength) in an individual, such as an older adult or an elderly individual. The method comprises administering to the individual an effective amount of adenosylcobalamin.

Yet another aspect of the present disclosure is a composition comprising adenosylcobalamin in an amount effective for weight management. "Weight management" for an adult (e.g., at least eighteen years from birth) means that the individual has approximately the same body mass index (BMI) after one week of consumption of the composition, preferably after one month of consumption of the composition, more preferably after one year of consumption of the composition, relative to their BMI when consumption of the composition was initiated. "Weight management" for younger individuals means that the BMI is approximately the same percentile relative to an individual of a corresponding age after one week of consumption of the composition, preferably after one month of consumption of the composition, more preferably after one year of consumption of the composition, relative to their BMI percentile when consumption of the composition was initiated. In some embodiments, the individual undergoing weight management is an overweight individual preventing obesity.

In a related embodiment, method of weight management in an individual comprises administering to the individual a composition comprising an effective amount of adenosylcobalamin.

The composition can improve physical endurance (e.g., ability to perform a physical task such as exercise, physical labor, sports activities), inhibit or retard physical fatigue, enhance blood oxygen levels, enhance energy in healthy individuals, enhance working capacity and endurance, reduce muscle fatigue, improve recovery from exercise, reduce stress, enhance function of cardiac muscle cells, improve sexual ability, increase muscle ATP levels, and/or reduce lactic acid in blood. "Endurance capacity" refers to the time to fatigue when exercising at a constant workload, generally at an intensity <80% $V0_2$max. In some embodiments, the composition is administered in an amount that increases mitochondrial activity, increases mitochondrial biogenesis, and/or increases mitochondrial mass.

A further aspect of the present disclosure is a composition comprising adenosylcobalamin in an amount effective to increase or maintain at least one of mitochondrial function or metabolic rate. In a related embodiment, a method of increasing or maintaining at least one of mitochondrial function or metabolic rate in an individual comprises administering to the individual a composition comprising an effective amount of adenosylcobalamin.

Yet another aspect of the present disclosure is a composition in a unit dosage form comprising adenosylcobalamin in an amount effective to treat, prevent, or manage at least one of a mitochondria-related disease, a condition associated with an altered mitochondrial function, or a reduced mitochondrial density. In a related embodiment, a method of treating an individual having at least one of a mitochondria-related disease, a condition associated with an altered mitochondrial function, or a reduced mitochondrial density comprises administering to the individual a composition comprising an effective amount of adenosylcobalamin. In another related embodiment, a method of preventing at least one of a mitochondria-related disease, a condition associated with an altered mitochondrial function, or a reduced mitochondrial density in an individual at risk thereof comprises administering to the individual a composition comprising an effective amount of adenosylcobalamin.

Another aspect of the present disclosure is a composition in a unit dosage form comprising adenosylcobalamin in an amount effective to improve or maintain cognitive function. In a related embodiment, a method of improving or maintaining cognitive function in an individual comprises administering to the individual a composition comprising adenosylcobalamin.

In an embodiment, the individual does not have a cognitive disorder. For example, the composition can enhance cognitive function in a subject having normal cognitive function.

The compositions disclosed herein can also be used in the treatment of any of a variety of additional diseases and conditions in which defective or diminished mitochondrial activity participates in the pathophysiology of the disease or condition, or in which increased mitochondrial function will yield a desired beneficial effect. Non-limiting examples of such conditions include male infertility associated with diminished sperm motility, macular degeneration and other age-related and inherited eye disorders, and hearing loss (e.g., age-related hearing loss).

In each of the compositions and methods disclosed herein, the adenosylcobalamin can be administered in a composition that is preferably a food product, including food additives, food ingredients, functional foods, dietary supplements, medical foods, nutraceuticals, or food supplements.

Dietary Intervention and Product

The term "dietary intervention" refers to an external factor applied to a subject which causes a change in the subject's diet. In one embodiment, the dietary intervention is a high calorie diet. In another embodiment, the dietary intervention is a high protein and/or carbohydrate diet. In another embodiment, the dietary intervention is a diet supplemented with vitamins and minerals.

In a preferred embodiment, the dietary intervention is a diet supplemented with adenosylcobalamin.

In another preferred embodiment, the dietary intervention is a diet supplemented with vitamin B12, in particular hydroxocobalamin and/or cyanocobalamin which can be converted into adenosylcobalamin.

The diet may be one which is adjusted to the starting body weight of the subject.

The dietary intervention may comprise administration of at least one diet product. The diet product may be a meal replacement product or a supplement product which may, for example, increase the subject's appetite. The diet product may include food products, drinks, pet food products, food supplements, nutraceuticals, food additives or nutritional formulas. Example oral nutritional supplements include Nestle Boost and Meritene products.

In an embodiment, the composition further comprises a medium-chain triglyceride, for example one or more of caproic acid, caprylic acid, capric acid and lauric acid. In an embodiment, the composition further comprises a phospholipid, for example phosphatidylcholine.

In an embodiment, the composition further comprises a source of protein, preferably purified protein (i.e., isolated from the native food ingredient in which it was created). The protein content of the composition is preferably 20-99 wt. % of the composition, for example 20-90 wt. % of the composition, for example, 30-80 wt. % of the composition, for example 40-80 wt. % of the composition, for example 50-80 wt. %, for example 40-70 wt. % of the composition.

Non-limiting examples of suitable protein or sources thereof for use in the compositions include hydrolyzed, partially hydrolyzed or non-hydrolyzed proteins or protein sources. They may be derived from any known or otherwise suitable source such as milk (e.g., casein, whey), animal (e.g., meat, fish), cereal (e.g., rice, corn) or vegetable (e.g., soy, pea) sources. Combinations of sources or types of proteins may be used. Non-limiting examples of proteins or sources thereof include intact pea protein, intact pea protein isolates, intact pea protein concentrates, milk protein isolates, milk protein concentrates, casein protein isolates, casein protein concentrates, whey protein concentrates, whey protein isolates, sodium or calcium casemates, whole cow's milk, partially or completely defatted milk, yoghurt, soy protein isolates and soy protein concentrates, and combinations thereof. Combinations of sources or types of proteins may be used. Preferred proteins include pea protein, whey protein, soy protein and casein. Casein proteins may, for example, comprise sodium caseinate and calcium caseinate.

The source of protein may be provided by individual amino acids, polypeptides comprising amino acids, or mixtures thereof. For many muscle growth, muscle maintenance and/or muscle enhancement treatments, particular amino acids beneficial, for example L-arginine, L-glutamine, lysine and the branched-chain amino acids (i.e. leucine, isoleucine, and valine; in particular leucine and isoleucine). These particular amino acids may be provided as the source of protein or they may be additional to a main source of protein. Thus, the source of protein in the composition may include one or more branched-chain amino acids (leucine, isoleucine, and valine); one or both of L-arginine and L-glutamine; and lysine. In a preferred embodiment, the composition comprises whey protein and/or casein protein together with one or more individual amino acids, for example one or more of (or all of) leucine, isoleucine and L-arginine.

The composition can be administered at least one day per week, preferably at least two days per week, more preferably at least three or four days per week (e.g., every other day), most preferably at least five days per week, six days per week, or seven days per week. The time period of administration can be at least one week, preferably at least one month, more preferably at least two months, most preferably at least three months, for example at least four months. In an embodiment, dosing is at least daily; for example, a subject may receive one or more doses daily. In some embodiments, the administration continues for the remaining life of the individual. In other embodiments, the administration occurs until no detectable symptoms of the medical condition remain. In specific embodiments, the administration occurs until a detectable improvement of at least one symptom occurs and, in further cases, continues to remain ameliorated.

The compositions disclosed herein may be administered to the subject orally, enterally or parenterally. Non-limiting examples of parenteral administration include intravenously, intramuscularly, intraperitoneally, subcutaneously, intraarticularly, intrasynovially, intraocularly, intrathecally, topically, and inhalation. As such, non-limiting examples of the form of the composition include natural foods, processed foods, natural juices, concentrates and extracts, injectable solutions, microcapsules, nano-capsules, liposomes, plasters, inhalation forms, nose sprays, nosedrops, eyedrops, sublingual tablets, and sustained-release preparations.

The compositions disclosed herein can use any of a variety of formulations for therapeutic administration. More particularly, pharmaceutical compositions can comprise appropriate pharmaceutically acceptable carriers or diluents and may be formulated into preparations in solid, semi-solid, liquid or gaseous forms, such as tablets, capsules, powders, granules, ointments, solutions, suppositories, injections, inhalants, gels, microspheres, and aerosols. As such, administration of the composition can be achieved in various ways, including oral, buccal, rectal, parenteral, intraperitoneal, intradermal, transdermal, and intratracheal administration. The active agent may be systemic after administration or may be localized by the use of regional administration, intramural administration, or use of an implant that acts to retain the active dose at the site of implantation.

In pharmaceutical dosage forms, the compounds may be administered as their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose functional derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional, additives such as solubilizers, isotonic agents, suspending agents, emulsifying agents, stabilizers and preservatives.

The compounds can be utilized in an aerosol formulation to be administered by inhalation. For example, the compounds can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds can be administered rectally by a suppository. The suppository can include a vehicle such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition. Similarly, unit dosage forms for injection or intravenous administration may comprise the compounds in a composition as a solution in sterile water, normal saline or another pharmaceutically acceptable carrier, wherein each dosage unit, for example, mL or L, contains a predetermined amount of the composition containing one or more of the compounds.

EXAMPLE

The following non-limiting example presents scientific data developing and supporting the concept of administering adenosylcobalamin to increase cellular energy production and thereby increase of function of different tissues.

Example 1

Material and Methods

To test the effect of adenosyl B12 and methyl B12 in human muscle myotubes, oxygen consumption rate and ATP production were measured in human myotubes, differentiated from primary adult muscle cells (HSMM). HSMM were purchased from Lonza (https://bioscience.lonza.com). HSMM were isolated from the upper arm or leg muscle tissue of normal donors and used after the second passage. HSMM were seeded in 96-well plates at a density of 12000 cells per well in SKM-M medium (ZenBio). Myotubes were differentiated from HSMM by growing the cells in DMEM/F-12 (Gibco) containing 2% horse serum, for 4 days. From the second growing day, the medium was not containing B12.

Oxygen consumption was measured using a XF96 instrument (Seahorse Biosciences, North Billerica, MA, USA). After differentiation, respiration rates were determined every 7 min at 37° C. Myotubes were stimulated with 10 μM epibatidine. Then, to measure the ATP-synthase-dependent component of the respiration, oligomycin (2.5 μg/ml) was added. ATP synthase-dependent respiration was calculated as the difference in respiration rate before and after the addition of oligomycin.

ATP measurements were carried out using myotubes infected with the adenovirus (from Sirion biotech) expressing luciferase. Luminescence was measured at the Cytation 3 cell imaging reader (Biotek). Relative changes of ATP were measured 48 h after infection in a luminometer, in standard medium containing 145 mM NaCl, 5 mM KCl, 1 mM $MgCl_2$, 1 mM $CaCl_2$), 10 mM glucose and 10 mM Hepes, pH 7.4. Luciferine (5 μM) was added to promote ATP-dependent reaction and basal luminescence was normalized as 100%. ATP production was stimulated in myotubes by addition of epibatidine.

For treatment, compounds were directly added to the cell culture or myotubes cultures 3 hours (acute treatment) or 3 days (chronic treatment) before measurements. Custom module analysis based on Excel (Microsoft) and GraphPad Prism 7.02 (GraphPad) software was used for quantification.

Results

Figure 2:
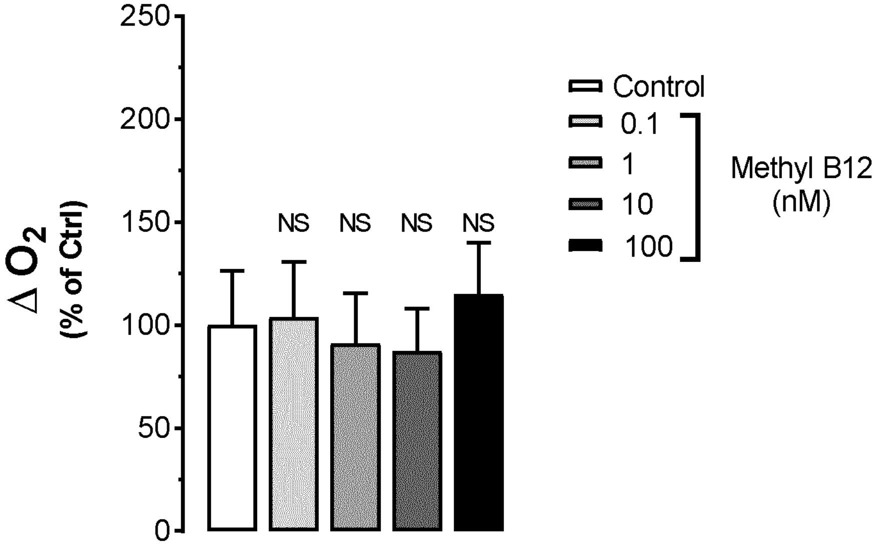

As shown in FIG. 1, Adenosyl B12 increases the ATP-synthase-dependent component of the respiration in stimulated human skeletal muscle myotubes, whereas methyl B12 (FIG. 2) does not increase the ATP-synthase-dependent component of the respiration in stimulated human skeletal muscle myoblasts.

Figure 3:
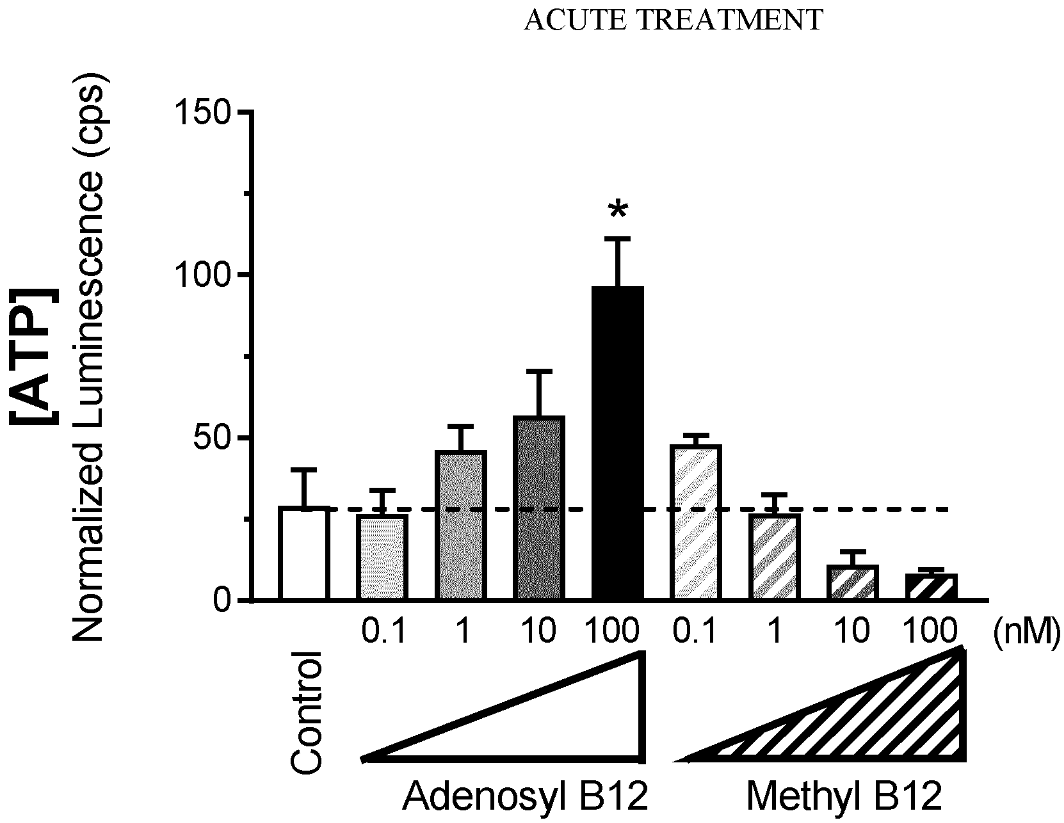

Similarly, as shown in FIG. 3. Adenosyl B12, but not methyl B12 potentiates epibatine-stimulated ATP production in human skeletal muscle myotubes, during acute treatment.

Figure 4:
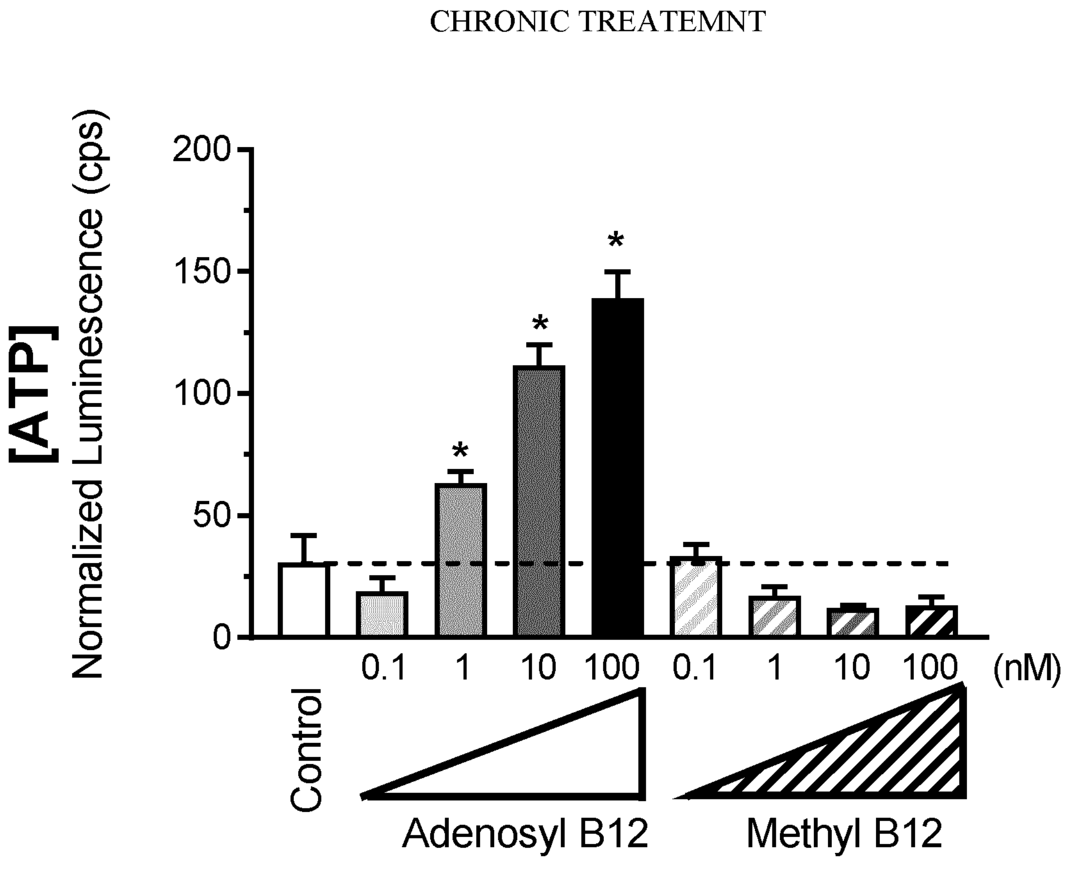

Also, chronic treatment of human skeletal muscle myotubes with Adenosyl B12, but not with methyl B12, potentiates epibatine-stimulated ATP production (FIG. 4).

Example 2

Material and Methods

Male Wistar rats aged 3 months or 19 months were treated with adenosylcobalamin (Adenosyl-B12) or methylcobalamin (Methyl-B12) at a dose of 1 mg/kg 3 times a week during 5 months by subcutaneous injection. Control animals were injected with equivalent volumes of saline. After 5 months treatment, adult rats were defined as 8 months old rats and old (aged) animals were defined as 24 old rodents.

Figure 5A:
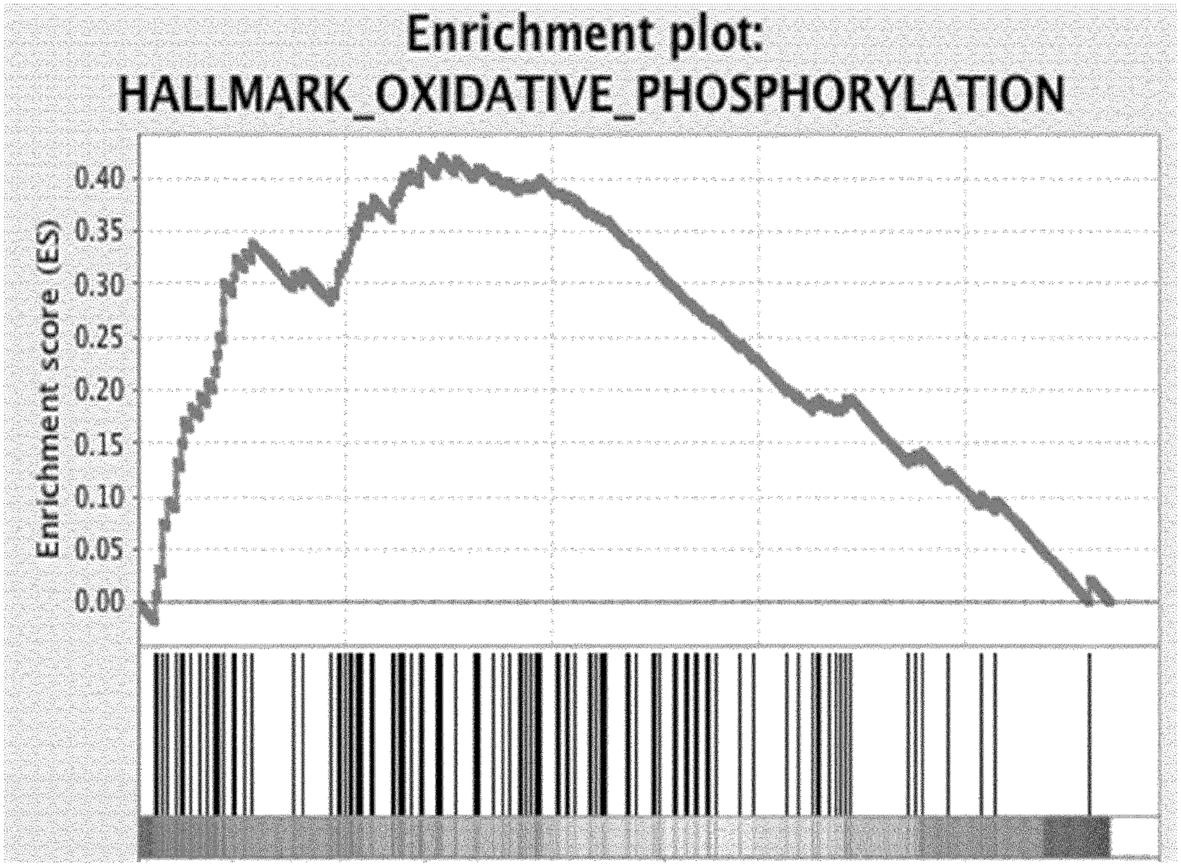
FIG. 5A: Enrichment plot analysis of skeletal muscle genes from old rats treated with Adenosyl-B12 vs old rats treated with Methyl-B12, showing the enrichment of the oxidative phosphorylation gene set.
Figure 5B:
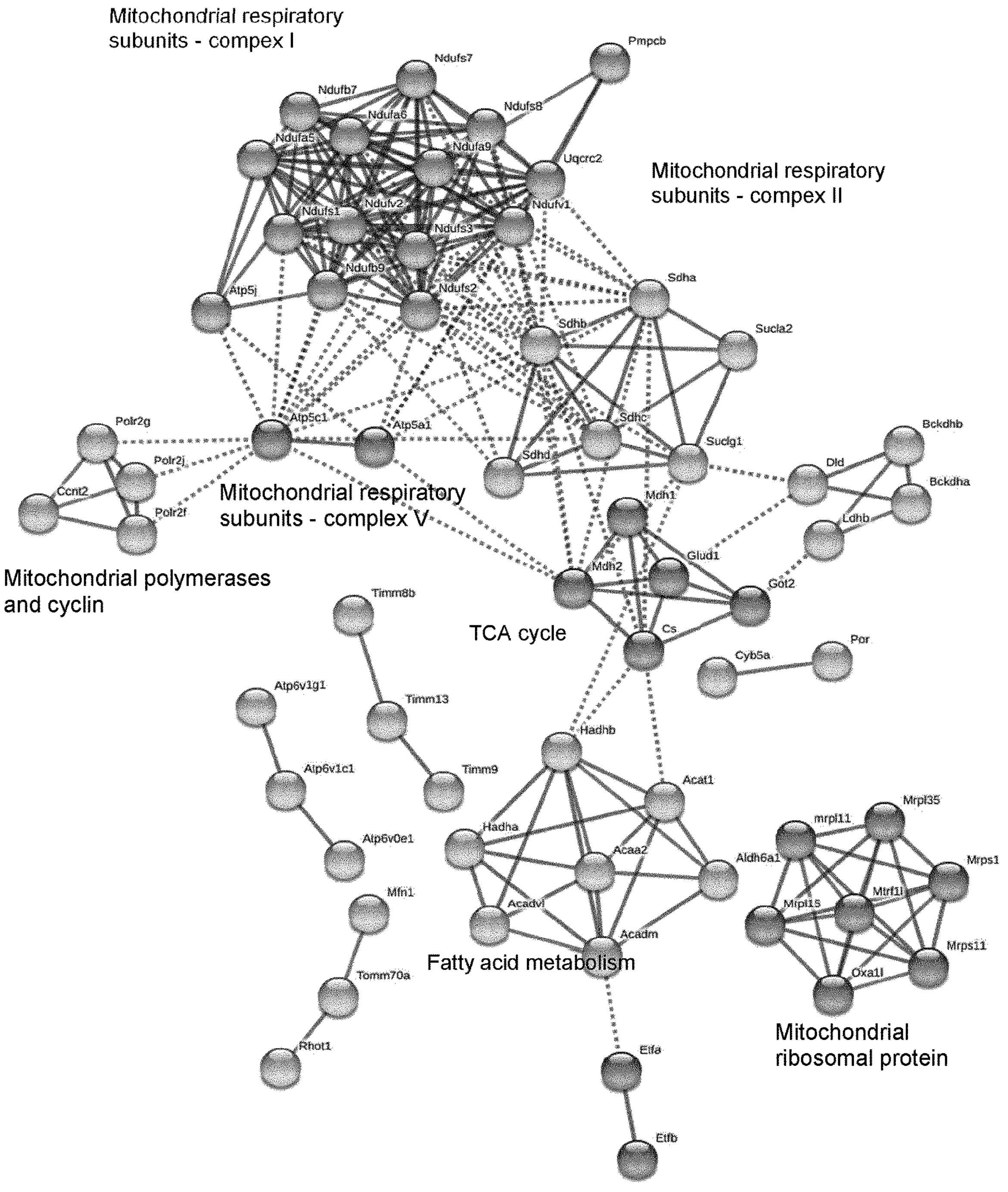
FIG. 5B: Network representation of the protein-protein interactions in skeletal muscle of old rats treated with Adenosyl-B12, showing that oxidative phosphorylation genes are differentially regulated. No network representation of oxidative phosphorylation genes is possible in animals treated with Methyl-B12.

Total RNA was extracted from tibialis anterior using the Agencourt RNAdvance Tissue Kit. For Gene-set enrichment analysis and Network analysis, RNA quantity was measured with Ribogreen and RNA quality was checked using the Standard Sensitivity RNA Analysis Kit on a Fragment Analyzer. All cRNA targets were synthesized using the IVT plus kit and fragmented according to the Affymetrix protocol, based on the Eberwine T7 procedure. Briefly, 100 ng of total RNA were used to produce double-stranded cDNA, followed by in vitro transcription, and cRNA labeling with biotin. Gene-set enrichment analysis (GSEA) of skeletal muscle describe the significant pathway differentially expressed (FIG. 5A). For Network analysis (FIG. 5B), nodes with an interaction score >0.9 are represented in different gray levels and aggregated by biological function.

Figure 6:
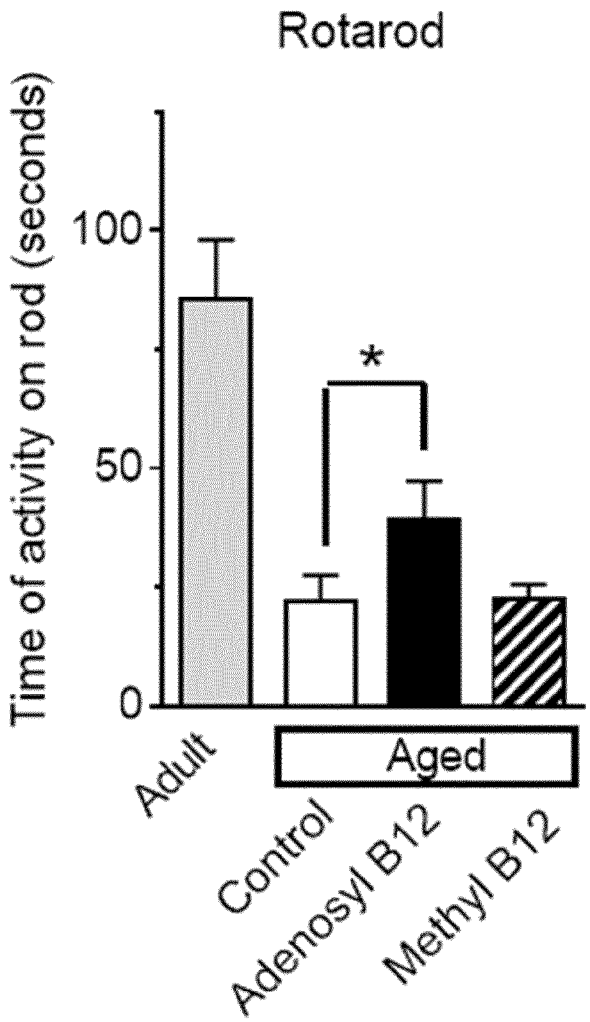
FIG. 6. Effect of Adenosyl-B12 on the time of activity on rod in aged rats. Results are expressed as mean+/−SEM, n=15. * indicates statistical significant difference vs. control cells (white) at $P<0.05$ ((Student's t-test)).

To determine muscle performance (FIG. 6), locomotor coordination was measured using rotarod device. Rats were placed on a rotating rod and the speed of rotation was gradually increased from 4 to 40 rpm over 600 sec, until the animal can no longer cope with the rotation and fell on a protected pad, placed below the rod. The time of activity on rotarod is measured in seconds. Each animal was recorded 3 times, with a resting period of at least 10 min between each trial.

Results

As shown in FIG. 5, Adenosyl-B12 specifically shows gene expression signature of oxidative phosphorylation genes in skeletal muscle. The enrichment plot analysis of the oxidative phosphorylation gene set of old rats treated in vivo with Adenosyl-B12 vs old rats treated with Methyl-B12 (panel 5A), indicates that mitochondrial energy production is a strong transcriptional signature of the Adenosyl-B12-treated skeletal muscle. In addition, network analysis of regulated genes (panel 5B) distinguished several clusters linked to mitochondrial respiratory chain complexes, oxidative phosphorylation and mitochondrial function, only in rats specifically treated with Adenosyl-B12.

Also, in vivo specific treatment of aged rats with Adenosyl B12 improves skeletal muscle performance, given that the time of activity on rod is significantly increased.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of treating, reducing an incidence of, and/or reducing a severity of a mitochondria-related disease or condition associated with altered mitochondrial function or reduced mitochondrial density, the method comprising orally administering to an individual in need thereof an effective amount of adenosylcobalamin, wherein the mitochondria-related disease or condition is selected from the group consisting of chronic kidney disease, orthopedic rehabilitation, macular degeneration, and combinations thereof.

2. The method of claim 1, wherein the amount of adenosylcobalamin is from 1 μg to 2000 μg per day.

3. The method of claim 1, wherein the adenosylcobalamin is in the form of a probiotic supplement comprising adenosylcobalamin-producing bacteria.

* * * * *